(12) United States Patent
Feng et al.

(10) Patent No.: US 10,883,146 B2
(45) Date of Patent: Jan. 5, 2021

(54) BIOMARKERS FOR RHEUMATOID ARTHRITIS AND USAGE THEREOF

(71) Applicant: BGI SHENZHEN, Guangdong (CN)

(72) Inventors: Qiang Feng, Guangdong (CN); Dongya Zhang, Guangdong (CN); Huijue Jia, Guangdong (CN); Donghui Wang, Guangdong (CN); Jun Wang, Guangdong (CN)

(73) Assignee: BGI SHENZHEN, Shenzhen (CN)

( * ) Notice: Subject to any disclaimer, the term of this patent is extended or adjusted under 35 U.S.C. 154(b) by 896 days.

(21) Appl. No.: 15/515,367

(22) PCT Filed: Jul. 7, 2015

(86) PCT No.: PCT/CN2015/083488
§ 371 (c)(1),
(2) Date: Mar. 29, 2017

(87) PCT Pub. No.: WO2016/050110
PCT Pub. Date: Apr. 7, 2016

(65) Prior Publication Data
US 2017/0226565 A1 Aug. 10, 2017

(30) Foreign Application Priority Data

Sep. 30, 2014 (WO) ............... PCT/CN2014/088060
Sep. 30, 2014 (WO) ............... PCT/CN2014/088068
Sep. 30, 2014 (WO) ............... PCT/CN2014/088069

(51) Int. Cl.
C12Q 1/689 (2018.01)
C12Q 1/6883 (2018.01)
A61K 35/747 (2015.01)
C07K 14/335 (2006.01)

(52) U.S. Cl.
CPC ............ *C12Q 1/689* (2013.01); *A61K 35/747* (2013.01); *C07K 14/335* (2013.01); *C12Q 1/6883* (2013.01); *C12Q 2600/118* (2013.01); *C12Q 2600/158* (2013.01)

(58) Field of Classification Search
None
See application file for complete search history.

(56) References Cited

FOREIGN PATENT DOCUMENTS

| JP | 2013183663 | 9/2013 |
| RU | 2362808 | 7/2009 |
| WO | 2014019267 | 2/2014 |

OTHER PUBLICATIONS

Holmes et al. Understanding the role of gut microbiome—host metabolic signal disruption in health and disease. Trends in MicrobiologyJul. 2011, vol. 19, No. 7, pp. 349-359 (Year: 2011).*

(Continued)

*Primary Examiner* — Olivia M. Wise
(74) *Attorney, Agent, or Firm* — Hodgson Russ LLP

(57) ABSTRACT

Biomarkers and methods for predicting risk of a disease in particular RA are provided. Sequences of DNA are obtained. The DNA may be extracted from a sample that is collected from a subject. A relative abundance of a biomarker is then calculated based on the sequences of the DNA. The biomarker comprises a DNA sequence in a genome of *Lactobacillus salivarius*. A probability of the subject having the disease is obtained based on the relative abundance.

3 Claims, 10 Drawing Sheets
Specification includes a Sequence Listing.

(56) References Cited

OTHER PUBLICATIONS

Gareau et al. Probiotics and the gut microbiota in intestinal health and disease. Nature Reviews Gastroenterology & Hepatology Sep. 2010, vol. 7, pp. 503-514 (Year: 2010).*
Qin et al. A metagenome-wide association study of gut microbiota in type 2 diabetes. Nature Oct. 2012, vol. 490,pp. 55-60 (Year: 2012).*
Said et al., "16s RDNA Analysis of the Salivary Microbiota Using 454 Pyrosequencing", Programme of the Annual Meeting of Japanese Molecular Biology Society, 2011, vol. 34, 2p-0087.
APO, Office Action for AU Application No. 2015327511, dated Mar. 28, 2018.
KIPO, Office Action for KR Application No. 20177011630, dated Apr. 30, 2018.
Junjie Qin et al., "A metagenome-wide association study of gut microbiota in type 2 diabetes", Nature, vol. 490, Oct. 4, 2012, Macmillan Publishers Limited, pp. 55-60.
Xiaofei Liu, et al., Analysis of Fecal Lactobacillus Community Structure in Patients with Early Rheumatoid Arthritis, Current Microbiology, vol. 67, No. 2, Mar. 13, 2013, pp. 170-176, Boston, USA.
Jimenez, E., et al., Lactobacillus salivarius CECT 5713, complete genome, Database Nucleotide, Jan. 31, 2014.

* cited by examiner

BIOMARKERS FOR RHEUMATOID ARTHRITIS AND USAGE THEREOF

CROSS-REFERENCE TO RELATED APPLICATIONS

The present patent application claims benefits of and priority to PCT Patent Application No. PCT/CN2014/088068, PCT/CN2014/088069 and PCT/CN2014/088060, each of which is filed Sep. 30, 2014, and incorporated herein by reference in its entireties.

TECHNICAL FIELD

The present disclosure relates to biomedical filed, and particularly to biomarkers and methods for predicting risk of a disease, in particular rheumatoid arthritis (RA).

BACKGROUND

Rheumatoid arthritis (RA) is a debilitating autoimmune disorder affecting tens of millions of people worldwide and increases mortality in the patients with its cardiovascular and other systemic complications. Despite success in alleviating the condition in many RA patients using disease-modifying antirheumatic drugs (DMARD), development of specific and more effective therapies has been hindered by insufficient understanding of factors that trigger or promote the disease. Investigation on microbiome may reveal probiotics that prevent or mitigate RA. Gut microbiota is a key environmental factor for human health, with established roles in obesity, diabetes, colon cancer, etc. Oral microbiota is relatively understudied compared to the gut microbiota. Metagenomic analysis of the role of oral microbiome in diseases has been lacking. It is also unknown that to what extent oral and gut microbial disease markers might converge in their identity or function.

SUMMARY

The present disclosure relates to biomedical filed, and particularly to biomarkers and methods for predicting risk of a disease, in particular rheumatoid arthritis (RA).

Disclosed in the present teaching are systems for obtaining a probability of a subject having a disease or evaluating a treatment regarding the disease.

In one example, a system for obtaining a probability of a subject having a disease is disclosed. The system comprises a processor and a storage medium containing program instructions for execution by the processor. The program instructions causing the processor to execute the following steps. A sample is collected from the subject. DNA is extracted from the sample. Sequences of the DNA are obtained. A relative abundance of a biomarker is then calculated based on the sequences of the DNA. The biomarker comprises a DNA sequence in a genome of *Lactobacillus salivarius*. A probability of the subject having the disease is obtained based on the relative abundance.

In another example, a system for evaluating a treatment regarding a disease or identifying therapeutic agents is disclosed. The system comprises a processor and a storage medium containing program instructions for execution by the processor. The program instructions causing the processor to execute the following steps. For each subject of a plurality of subjects having the disease, first DNA sequences extracted from a first sample and second DNA sequences extracted from a second sample are obtained. The first sample is collected from the subject before the subject receives the treatment. The second sample is collected from the subject after the subject receives the treatment. For each subject, a first relative abundance of a biomarker is calculated based on the first DNA sequences; and a second relative abundance of the biomarker is calculated based on the second DNA sequences. The biomarker comprises a DNA sequence in genome of *Lactobacillus salivarius*. The treatment is then evaluated based on the first relative abundances and the second relative abundances calculated for the plurality of subjects.

In a different example, a system for evaluating a treatment regarding a disease or identifying therapeutic agents is disclosed. The system comprises a processor and a storage medium containing program instructions for execution by the processor. The program instructions causing the processor to execute the following steps. For each subject of a plurality of subjects having the disease, sequences of DNA are obtained, where the DNA may be extracted from a sample that is collected from the subject after the subject receives the treatment; and a relative abundance of a biomarker is calculated based on the sequences of the DNA. The biomarker comprises a DNA sequence in genome of *Lactobacillus salivarius*. The treatment is then evaluated based on the relative abundances calculated for the plurality of subjects.

Also disclosed in the present teaching are methods for obtaining a probability of a subject having a disease or evaluating a treatment regarding the disease or identifying therapeutic agents.

In one example, a method is disclosed. A sample is collected from a subject. DNA is extracted from the sample. Sequences of the DNA are obtained. A relative abundance of a biomarker is then calculated based on the sequences of the DNA. The biomarker comprises a DNA sequence in a genome of *Lactobacillus salivarius*. A probability of the subject having a disease is obtained based on the relative abundance.

In another example, a method for evaluating a treatment regarding a disease or identifying therapeutic agents is disclosed. For each subject of a plurality of subjects having the disease, first DNA sequences extracted from a first sample and second DNA sequences extracted from a second sample are obtained. The first sample is collected from the subject before the subject receives the treatment. The second sample is collected from the subject after the subject receives the treatment. For each subject, a first relative abundance of a biomarker is calculated based on the first DNA sequences; and a second relative abundance of the biomarker is calculated based on the second DNA sequences. The biomarker comprises a DNA sequence in genome of *Lactobacillus salivarius*. The treatment is then evaluated based on the first relative abundances and the second relative abundances calculated for the plurality of subjects.

In a different example, a method for evaluating a treatment regarding a disease or identifying therapeutic agents is disclosed. For each subject of a plurality of subjects having the disease, sequences of DNA are obtained, where the DNA may be extracted from a sample that is collected from the subject after the subject receives the treatment; and a relative abundance of a biomarker is calculated based on the sequences of the DNA. The biomarker comprises a DNA sequence in genome of *Lactobacillus salivarius*. The treatment is then evaluated based on the relative abundances calculated for the plurality of subjects.

Also disclosed in the present teaching is a computer program product for obtaining a probability of a subject having a disease. The computer program product comprises a computer-readable storage medium having program code stored thereon. The program code is executable by a processor and comprises instructions to cause the processor to execute the following steps. A sample is collected from the subject. DNA is extracted from the sample. Sequences of the DNA are obtained. A relative abundance of a biomarker is then calculated based on the sequences of the DNA. The biomarker comprises a DNA sequence in a genome of *Lactobacillus salivarius*. A probability of the subject having the disease is obtained based on the relative abundance.

Also disclosed in the present teaching is a biomarker for obtaining a probability of a subject having a disease or evaluating a treatment regarding the disease or identifying therapeutic agents. The biomarker comprises at least one DNA sequence in a genome of *Lactobacillus salivarius* or at least one of the following metagenomic linkage groups (MLGs): MLG consisting of MLG ID NO: 2169; MLG consisting of MLG ID NO: 16600; and MLG consisting of MLG ID NO: 4643.

Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF THE DRAWINGS

The methods and systems described in the present teaching are further described in terms of exemplary embodiments. These exemplary embodiments are described in detail with reference to the drawings. These exemplary embodiments are non-limiting exemplary embodiments, in which like reference numerals represent similar structures throughout the several views of the drawings, and wherein.

DETAILED DESCRIPTION

Terms used herein have meanings as commonly understood by a person of ordinary skill in the areas relevant to the present teaching. Terms such as "a", "an" and "the" are not intended to refer to only a singular entity, but include the general class of which a specific example may be used for illustration. The terminology herein is used to describe one or more exemplary embodiments of the present teaching, but their usage does not delimit the present teaching, except as outlined in the claims.

The present disclosure describes biomarkers and methods for utilizing the biomarkers to predict risk of a disease and determine an effect of a treatment regarding the disease, in particular the disease of RA. Infectious agents have long been implicated with RA. However, identity and pathogenicity of the RA-associated agent(s) have been largely unclear, a question further complicated by a recent reinstatement that human body is a super-organism hosting trillions of beneficial as well as harmful microorganisms.

RA is believed to initiate and lurk in some other body site(s) for years before the onset of joint inflammation. Investigation on microbiome may reveal probiotics that prevent or mitigate RA. Gut microbiota is a key environmental factor for human health, with established roles in obesity, diabetes, colon cancer, etc. Besides functioning in nutrient and xenobiotic metabolism, microbes in distal gut crosstalk with neuro-immune-endocrine system and blood stream to impact the entire human body. The gut microbiota is stably associated with a given individual, adding to its value in disease-related investigations. The heterogeneity of the gut microbiome in the human population suggests that treatment of diseases should be personalized according to the gut microbiome, whose role in drug activation or inactivation, immune modulation, etc. remains largely unclear. Oral microbiota is relatively understudied compared to the gut microbiota, with the Human Microbiome Project (HMP) only sampling ~100 healthy individuals for WGS (whole genome sequencing). Metagenomic analysis of the role of the oral microbiome in diseases has been lacking, despite that dental and salivary samples are more readily available at clinical visits than fecal samples. It is also unknown that to what extent oral and gut microbial disease markers might converge in their identity or function.

A biomarker generally refers to a measurable indicator of some biological state or condition. The term "biomarker" as used in the present teaching refers to a measurable substance in an organism whose presence is indicative of some phenomenon such as disease, infection, or environmental exposure. In particular, a biomarker in a sample from a RA patient or a normal person may be utilized to evaluate RA risk of the person.

Figure 1:
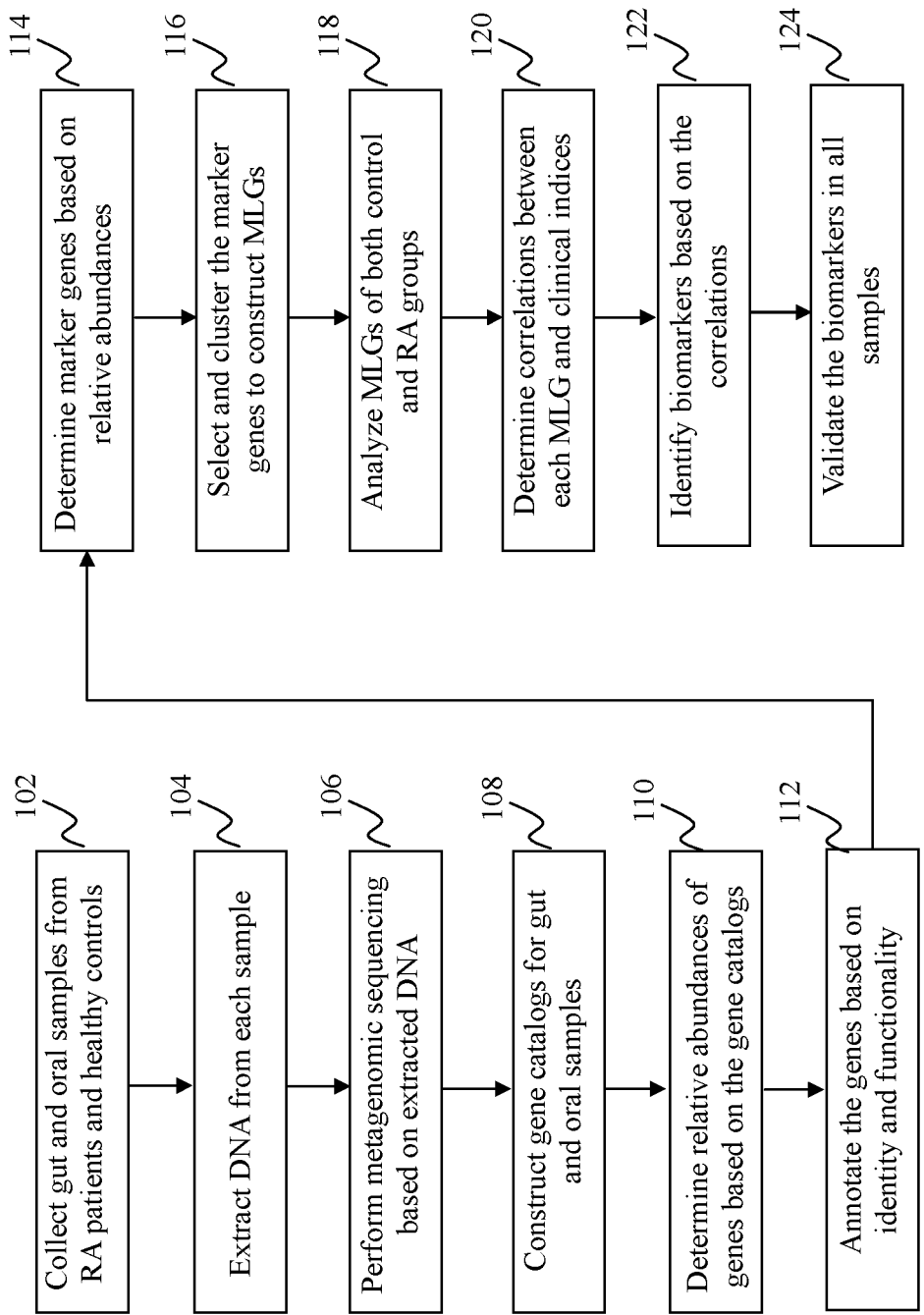
FIG. 1 shows a flowchart of an exemplary process in which biomarkers are identified and validated for evaluating RA risk, according to an embodiment of the present teaching.

FIG. 1 shows a flowchart of an exemplary process in which biomarkers are identified and validated for evaluating RA risk, according to an embodiment of the present teaching. First, gut and/or oral samples are collected at 102 from both RA patients and healthy control people. The gut samples may include fecal samples, while the oral samples may include dental and salivary samples. DNA extraction is performed on each sample at 104. The extracted DNA is sequenced, e.g. by a metagenomic sequencing, at 106. Then at 108, gene catalogs are constructed for gut and oral samples. The gene catalog for gut samples may be replaced or integrated with an existing gene catalog, while there is few existing gene catalog for oral samples.

Based on the gene catalogs, at 110, relative abundances of genes in the samples are determined. A relative abundance of a given gene in a sample can be calculated as below. First, the copy number of each gene in the sequenced data from the sample is calculated as a ratio between the times which a gene can be detected in the sample and the length of the gene. Second, the relative abundance of the given gene can be calculated as a ratio between the copy number of the given gene and a summation of the copy numbers of all genes in the sample.

At 112, the genes are annotated based on their identities and functionalities. Marker genes can be determined at 114 based on their respective relative abundances, e.g. when a marker gene shows difference in relative abundances between control and RA groups. These marker genes are selected and clustered at 116 to construct MLGs. The term "MLG" as used in the present teaching may refer to a group of genetic material in a metagenome that is probably physically linked as a unit rather than being independently distributed. At 118, the MLGs of both control and RA groups are analyzed. Correlations between each MLG and clinical indices are determined at 120. At 122, one or more biomarkers are identified from the MLGs based on the correlations, e.g. when a biomarker shows positive correlation with a predominant antibody of the mucosal immune system or with a major serum immunoglobulin. At 124, the biomarkers are validated in all samples. For example, a biomarker may be validated if it is consistently found enriched in gut and/or oral samples from the RA patients.

According to an embodiment of the present disclosure, a validated biomarker comprises a DNA sequence in a genome of *Lactobacillus salivarius*. According to various embodiments of the present disclosure, the validated biomarker may comprise at least a partial sequence of SEQ ID NO: 1 to 593; SEQ ID NO: 594 to 1536; or SEQ ID NO: 1537 to 2594, as stated in Table 2-2. A sequence listing submitted herewith includes nucleotide and/or amino acid sequences corresponding to the above mentioned SEQ IDs.

For example, referring to Table 2-2, MLG ID NO: 2169 contains at least 593 RA-associated genes identified from fecal samples. These 593 genes have the polynucleotide sequences of SEQ ID NOs: 1~593, respectively. As understood by those skilled in the art, MLG ID NO: 2169 may contain other genes in addition to SEQ ID NOs: 1~593. In an embodiment of the present teaching, at least 80% (such as at least 80%, 85%, 90%, 95% or 100%) of the genes of MLG ID NO: 2169 have at least 85% (such as at least 85%, 90%, 95% or 100%) sequence identity to the polynucleotide sequences of SEQ ID NOs: 1~593 and encode polypeptides having at least 85% (such as at least 85%, 90%, 95% or 100%) sequence identity to the amino acid sequences encoded by SEQ ID NOs: 1~593. In another embodiment of the present teaching, MLG ID NO: 2169 consists of genes having the polynucleotide sequences of SEQ ID NOs: 1~593.

Similarly, referring to Table 2-2, MLG ID NO: 16600 contains at least 943 RA-associated genes identified from fecal samples. These 943 genes have the polynucleotide sequences of SEQ ID NOs: 594~1536, respectively. As understood by those skilled in the art, MLG ID NO: 16600 may contain other genes in addition to SEQ ID NOs: 594~1536. In an embodiment of the present teaching, at least 80% (such as at least 80%, 85%, 90%, 95% or 100%) of the genes of MLG ID NO: 16600 have at least 85% (such as at least 85%, 90%, 95% or 100%) sequence identity to the polynucleotide sequences of SEQ ID NOs: 594~1536 and encode polypeptides having at least 85% (such as at least 85%, 90%, 95% or 100%) sequence identity to the amino acid sequences encoded by SEQ ID NOs: 594~1536. In another embodiment of the present teaching, MLG ID NO: 16600 consists of genes having the polynucleotide sequences of SEQ ID NOs: 594~1536.

Similarly, referring to Table 2-2, MLG ID NO: 4643 contains at least 1058 RA-associated genes identified from fecal samples. These 1058 genes have the polynucleotide sequences of SEQ ID NOs: 1537~2594, respectively. As understood by those skilled in the art, MLG ID NO: 4643 may contain other genes in addition to SEQ ID NOs: 1537~2594. In an embodiment of the present teaching, at least 80% (such as at least 80%, 85%, 90%, 95% or 100%) of the genes of MLG ID NO: 4643 have at least 85% (such as at least 85%, 90%, 95% or 100%) sequence identity to the polynucleotide sequences of SEQ ID NOs: 1537~2594 and encode polypeptides having at least 85% (such as at least 85%, 90%, 95% or 100%) sequence identity to the amino acid sequences encoded by SEQ ID NOs: 1537~2594. In another embodiment of the present teaching, MLG ID NO: 4643 consists of genes having the polynucleotide sequences of SEQ ID NOs: 1537~2594.

The present teaching is further exemplified in the following non-limiting examples. Unless otherwise stated, parts and percentages are by weight and degrees are Celsius. As apparent to one of ordinary skill in the art, these examples, while indicating preferred embodiments of the present teaching, are given by way of illustration only, and the agents are all commercially available.

The examples relate to methods for identifying and validating biomarkers for evaluating RA risk. In one example, metagenomic shotgun sequencing was performed for 212 fecal samples (77 treatment-naive RA cases, 80 unrelated healthy controls; 17 treatment-naive RA cases and 17 related healthy controls; 21 DMARD-treated cases) (Tables 1-1, 1-2, 1-3). This may be used to investigate the gut microbiome in RA patients. The data were then integrated into an existing gut microbial reference gene catalog to obtain a set of 5.9 million genes (from 481 samples), which allowed saturating mapping of the sequencing reads (80.3±2.3%, mean±s.d.) (Li, J. et al. An integrated catalog of reference genes in the human gut microbiome. Nat. Biotechnol. (2014), incorporated herein by reference).

Dental plaques and saliva were also sampled from treatment-naive RA patients and healthy controls, and performed metagenomic sequencing on the 105 dental and 98 saliva samples (dental/salivary samples from 54/51 treatment-naive RA cases and 51/47 healthy controls; 69 of the subjects having the complete set of fecal, dental and salivary samples) (Tables 1-1, 1-2, 1-3). This may show that dysbiosis is also evident in the oral microbiome, after demonstrating the dysbiosis in the RA gut microbiome. De novo assembly of these sequences led to a gene catalog of 3.2 million genes, with 76.6±1.8% and 70.7±7.3% (mean±s.d.) mapping of the dental and salivary sequencing reads, respectively.

Study cohort is described as below. RA was diagnosed at Peking Union Medical College Hospital according to the 2010 ACR/EULAR (American College Of Rheumatology/ European League Against Rheumatism) classification criteria. All phenotypic information was collected upon the subjects' initial visit to the hospital following standard procedures. 21 fecal samples from DMARD-treated patients were only included in the 212 samples used for gut microbial gene catalog construction, and were not analyzed in this example. RA patients were between 18 and 65 years old, with disease duration of at least 6 weeks, at least 1 swollen joint and 3 tender joints enlisted. Patients were excluded if they had a history of chronic serious infection, any current infection or any type of cancer. Pregnant or lactating women were excluded. All patients were informed of the risk of infertility and patients with a desire to have children were excluded. Even though some of the patients had suffered from RA for years, they were DMARD-naïve because they had not been diagnosed with RA at local hospitals before visiting Peking Union Medical College Hospital, and had only taken painkillers to relieve RA symptoms.

The healthy control group met the following inclusion criteria: 18-65 years of age; having a normal level on recently screening for liver and kidney function, routine blood test, erythrocyte sedimentation rate, fasting blood glucose, blood lipid, and blood pressure. Subjects were excluded if they had a history of chronic serious infection, any current infection, any type of cancer or autoimmune disease. Pregnant or lactating women were excluded. Subjects who had received antibiotic treatment within 1 month before participating in this study were also excluded.

The treatment was performed with methotrexate (MTX)-based DMARDs. 97% of the patients received MTX alone (7.5 mg QW initially, 15 mg (max 0.3 mg/kg) QW from 4 weeks and on; supplemented with 10 mg QW folate), T2 alone (20 mg TID), or MTX plus T2. Other drugs used on the remaining patients included Leflunomide (LEF), prednisolone (pred), hydroxychloroquine (HCQ) and etanercept, which were not compared due to the small sample size. As used in the present teaching, "QW" means once a week; "TID" means three times a day; and "T2" means *Tripterygium wilfordii* (thunder god vine) glycosides. Based on reduction in DAS28-ESR after treatment, the patient samples were divided into good, moderate and no improvement, according to the EULAR response criteria. As patients from all over China came to visit Peking Union Medical College Hospital, not all patient samples were available after treatment.

The study was approved by the institutional review boards at Peking Union Medical College Hospital and (Beijing Genomics Institute) BGI-Shenzhen.

Sample collection is described as below. Fecal samples were collected at Peking Union Medical College Hospital, transported frozen, and extracted at BGI-Shenzhen as previously described (Qin, J. et al. A metagenome-wide association study of gut microbiota in type 2 diabetes. Nature 490, 55-60 (2012), incorporated herein by reference). Dental plaques were scraped from dental surfaces using ophthalmology forceps until there was 3 µl of volume. The sample was transferred into 2000 of 1× lysis buffer containing 10 mM Tris, 1 mM EDTA (Ethylene Diamine Tetraacetic Acid), 0.5% Tween 20 and 200 µg/ml proteinase K (Fermentas) and incubated for 2 hours at 55° C. Lysis was terminated by incubation at 95° C. for 10 minutes, and the sampled were frozen at −80° C. until transport. DNA extraction was performed following the protocol for fecal samples. For saliva, 100 µl of saliva was added into 100 µl of 2× lysis buffer. The posterior pharynx wall was swabbed and added to the same tube. The samples were then lysed and extracted as the dental samples.

All available samples were analyzed (Tables 1-1, 1-2, 1-3). Some of the fecal samples were excluded due to constipation, or inappropriate sample preservation; some of the oral samples were excluded due to low concentration of microbial DNA.

Metagenomic sequencing and assembly is described as below. Paired-end metagenomic sequencing was performed on the Illumina platform (insert size 350 bp, read length 100 bp), and the sequencing reads were quality-controlled and de novo assembled into contigs using SOAPdenovo v2.04 (Luo, R. et al. SOAPdenovo2: an empirically improved memory-efficient short-read de novo assembler. Gigascience 1, 18 (2012), incorporated herein by reference), as described previously (Qin et al. 2012, supra). The average rate of host contamination was 0.37% for fecal, 5.55% for dental and 40.85% for saliva samples.

Gene catalog construction is described as below. Gene prediction from the assembled contigs was performed using GeneMark v2.7d. Redundant genes were removed using BLAT with the cutoff of 90% overlap and 95% identity (no gaps allowed), resulting in a non-redundant gene catalog of 3,800,011 genes for 212 fecal samples (containing 21 of the DMARD-treated samples), and a catalog of 3,234,997 genes for the 203 treatment-naïve oral samples (105 dental plaques samples and 98 saliva samples). The gene catalog from fecal samples was further integrated into an existing gut microbial reference catalog of 4.3 million genes using BLAT (95% identity, 90% overlap) (Qin et al. 2012, supra), resulting in a final catalog of 5.9 million genes. Relative abundances of the genes were determined by aligning high-quality sequencing reads to the gut or oral reference gene catalog. A detailed procedure for the aligning can be found in Qin et al. 2012, supra.

Taxonomic annotation and abundance calculation are described as below. Taxonomic assignment of the predicted genes was performed according to the IMG database (v400) based on an in-house pipeline detailed previously (Qin et al. 2012, supra), with 70% overlap and 65% identity for assignment to phylum, 85% identity to genus, and 95% identity to species. The relative abundance of a taxon was calculated from the relative abundance of its genes.

In one example, a relative abundance of a given gene in a sample can be calculated as below. First, the copy number of each gene in the sequenced data from the sample is calculated as a ratio between the times which a gene can be detected in the sample (i.e. the number of mapped reads) and the length of the gene. Second, the relative abundance of the given gene can be calculated as a ratio between the copy number of the given gene and a summation of the copy numbers of all genes in the sample.

Significant differences in relative abundance of a taxon between patients and healthy controls were identified by a Wilcoxon rank-sum test with $p<0.05$.

Metagenome-wide association study (MGWAS) is described as below. For case-control comparison of the fecal microbiome, removal of genes detected in less than 10% of the samples led to a set of 2,007,643 genes. 117,219 genes showed differences in relative abundance between controls and cases (Wilcoxon rank-sum test, FDR<0.3). These marker genes were then clustered into MLGs according to their abundance variation across all samples (Qin et al. 2012, supra). MLG is a generalized concept in lieu of a species concept for a metagenome. The term "MLG" as used in the present teaching may refer to a group of genetic material in a metagenome that is probably physically linked as a unit rather than being independently distributed. This may help to avoid the need to completely determine the specific microbial species present in the metagenome, which is important given that there are a large number of unknown organisms and that there is frequent lateral gene transfer (LGT) between bacteria. MLG can be used to reduce and structurally organize the abundant metagenomic data and to help making a taxonomic description. Based a gene profile, a MLG can be identified as a group of genes that co-exists among different individual samples and has a consistent abundance level and taxonomic assignment.

For constructing dental MLGs, 371990 marker genes (Wilcoxon rank-sum test, FDR<0.1) were selected from 1900774 genes (present in at least 10% of the samples). For salivary MLGs, 258055 marker genes (Wilcoxon rank-sum test, FDR<0.1) were selected from 2030636 genes (present in at least 10% of the samples).

Taxonomic assignment and abundance profiling of the MLGs were performed according to the taxonomy and the relative abundance of their constituent genes, as previously described (Qin et al. 2012, supra). All genes from one MLG were aligned to the reference microbial genomes at the nucleotide level and the (National Center for Biotechnology Information) NCBI-nr database at the protein level. From the alignments with the reference microbial genomes, one can obtain a list of well-mapped bacterial genomes for each MLG and order these bacterial genomes according to the proportion of genes that could be mapped onto the bacterial genome, as well as the average identity of the alignments.

Assignment to species may require more than 90% of genes in an MLG to align with the species' genome with more than 95% identity, 70% overlap of query. Assigning an MLG to a genus may require more than 80% of its genes to align with a genome with 85% identity in both DNA and protein sequences.

MLGs were further clustered according to Spearman's correlation between their abundances in all samples regardless of case-control status.

Correlation of MLGs from different body sites is analyzed in the same manner in the 69 subjects (36 controls, 33 treatment-naïve cases) having fecal, dental and salivary samples.

Canonical correspondence analysis (CCA) was performed on the MLG abundance profile of the control and RA samples to assess the impact from each of the factors listed (Feng, Q. et al. Gut microbiome development along the colorectal adenoma carcinoma sequence. Nat. Commun. 6, 6528 (2015), incorporated herein by reference in its entirety).

117,219 gene markers differentially enriched in RA patients or controls (Wilcoxon rank-sum test, FDR<0.3) were identified. This may help to accurately delineate features of the RA-associated gut microbiota. Metagenomic linkage groups (MLGs) were computed based on abundance covariations between the genes among samples (Qin et al. 2012, supra). The 88 MLGs that contained at least 100 genes were separated according to their direction of enrichment in canonical coordinate analysis (CCA), confirming that they were mainly associated with the RA status.

The 171 dental and 142 salivary MLGs that contained at least 100 genes were separated according to their direction of enrichment in CCA, confirming their association with RA.

Association between MLGs and clinical indices is described as below. Spearman's correlation was performed between the relative abundance of each MLG and continuous variables measured clinically, as previously described (Karlsson, F. H. et al. Gut metagenome in European women with normal, impaired and diabetic glucose control. Nature 498, 99-103 (2013), incorporated herein by reference in its entirety).

Numerical covariations were investigated between the relative abundance of the MLGs and the clinical indices using Spearman's correlation. This may help to explore the diagnostic or prognostic value of the gut microbiome for RA.

In one example, the relative abundance of a MLG in a sample can be estimated based on the relative abundance values of genes from this MLG. For this MLG, one may discard genes that were among the 5% with the highest and lowest relative abundance, respectively, and then fit a Poisson distribution to the rest. The estimated mean of the Poisson distribution can be interpreted as the relative abundance of this MLG. The profile of MLGs among all samples may be obtained for further analyses. The relative abundance of a biomarker in a sample may be calculated in a similar way.

Figure 2:
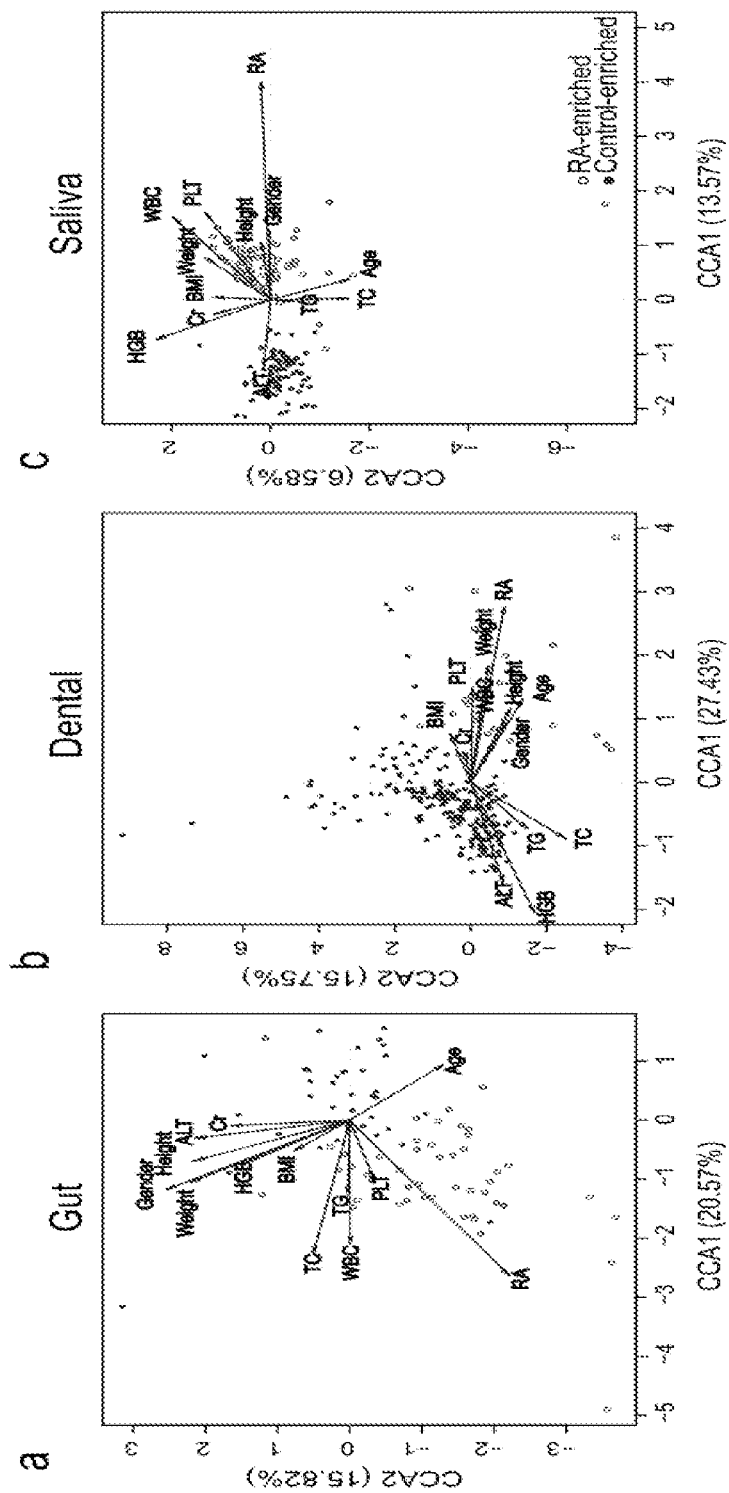
FIG. 2 illustrates analysis results for influence of phenotypes on gut, dental, and salivary metagenomic linkage groups (MLGs), according to an embodiment of the present teaching.

FIG. 2 illustrates analysis results for influence of phenotypes on gut, dental, and salivary MLGs, according to an embodiment of the present teaching. In this example, FIG. 2 shows CCA result for influence of phenotypes on the gut (a), dental (b) or salivary (c) MLGs. Categorical or continuous phenotypes missing in half of the samples were not analyzed. Solid points represent control-enriched MLGs, while hollow points represent RA-enriched MLGs. RA-enriched MLGs, e.g. *Clostridium asparagiforme*, *Bacteroides* sp. and *Lactobacillus* sp. (most related to *L. salivarius*, Table 2-1, Table 2-2) were correlated positively with the predominant antibody of the mucosal immune system, IgA, or with the major serum immunoglobulin, IgG.

Meanwhile, anaerobes such as *Lactobacillus salivarius*, *Atopobium* sp. and *Cryptobacterium curtum* were found in both the salivary and dental samples of the RA patients.

Assembly of more RA-relevant genomes is described as below. One can then assemble bacterial genomes directly from MLGs and its associated metagenomic sequencing reads using a software package in the SOAP (short oligonucleotide alignment program) family, e.g. SOAPMeta (patent application PCT/CN2012/079492, incorporated herein by reference). For *Lactobacillus* sp. (most related to *Lactobacillus salivarius*), the assembly was sufficiently complete after a single round of advanced assembly using data from a RA patient (Table 3), and showed colinearity with the *Lactobacillus salivarius* CECT (Coleccion Espanola de Cultivos Tipo) 5713 reference genome.

Figure 3:
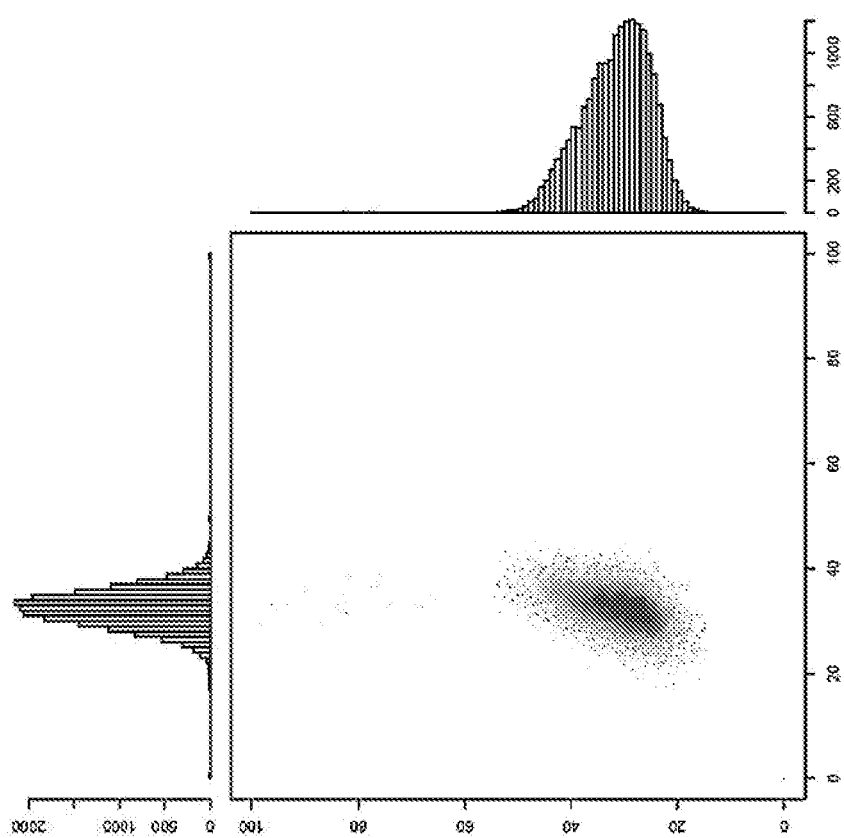
FIG. 3 shows a GC-depth graph for *Lactobacillus* sp. after advanced assembly, according to an embodiment of the present teaching.
Figure 4:
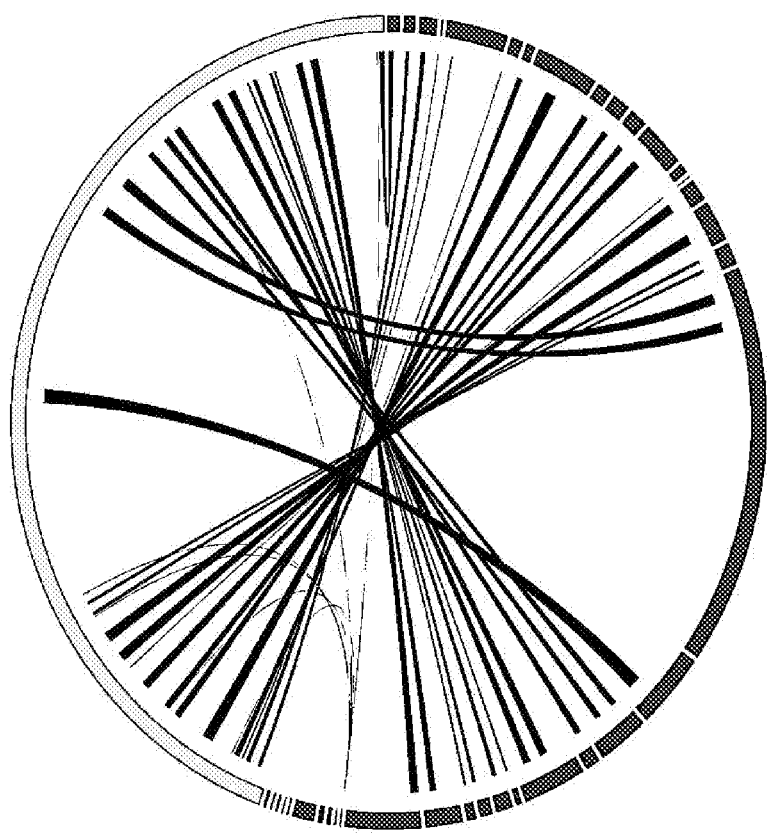
FIG. 4 shows co-linearity between an assembly and *Lactobacillus salivarius*, according to an embodiment of the present teaching.

FIG. 3 and FIG. 4 show *Lactobacillus* sp. draft genome. FIG. 3 shows a GC-depth graph for *Lactobacillus* sp. after advanced assembly, according to an embodiment of the present teaching. FIG. 4 shows co-linearity between the assembly (from sample D201) and the *Lactobacillus salivarius* CECT 5713 reference draft genome from NCBI (NC_017481.1), according to an embodiment of the present teaching. Functions encoded by the genome were largely similar to those in *Lactobacillus salivarius* CECT 5713 or other *Lactobacillus* strains, except that this RA-enriched *Lactobacillus* sp. encodes different cell wall modifications which might be recognized by the host immune system.

Concordance between the gut and oral microbiome is described as below. Despite differences between the gut and oral bacterial taxa associated with RA, *Lactobacillus salivarius* was consistently found to be enriched in the RA patients, the gut and salivary MLGs were positively correlated with IgG, and the dental *L. salivarius* showed the second highest odds ratio among all dental MLGs (Table 2-1). These results make them strong candidates as biomarkers for RA. Furthermore, *L. salivarius* was more abundant in very active (DAS28>5.1) RA cases compared to mild-to-moderately active (DAS28≤5.1) RA cases (Table 4, p=0.017, 0.036, 0.084 in feces, dental plaques and saliva, respectively, Wilcoxon rank-sum test), underscoring its potential for non-invasive prognosis.

According to an embodiment of the present disclosure, a biomarker for evaluating or diagnosing RA comprises a DNA sequence in a genome of *Lactobacillus salivarius*. According to various embodiments of the present disclosure, the biomarker for evaluating or diagnosing RA may comprise at least a partial sequence of SEQ ID NO: 1 to 593; SEQ ID NO: 594 to 1536; or SEQ ID NO: 1537 to 2594, as stated in Table 2-2. The sequence listing submitted herewith includes nucleotide and/or amino acid sequences corresponding to the above mentioned SEQ IDs.

Figure 5:
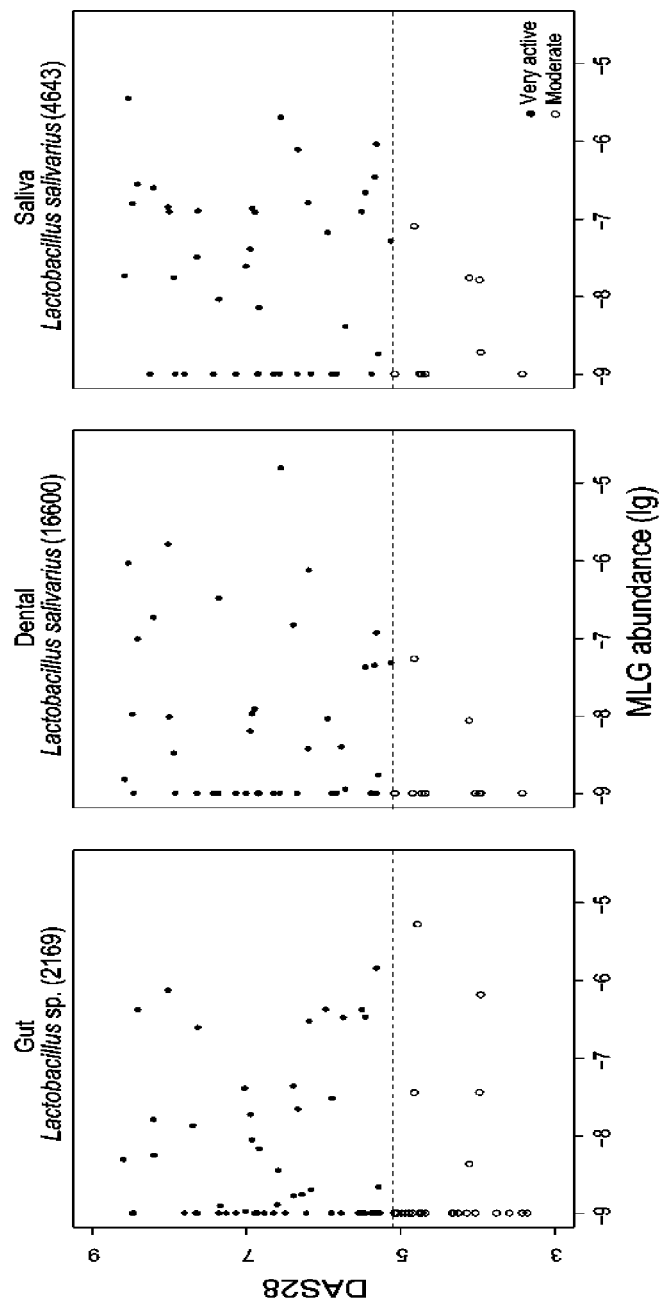
FIG. 5 shows patient stratification based on a RA-associated bacterium, according to an embodiment of the present teaching.

FIG. 5 shows patient stratification based on a RA-associated bacterium, according to an embodiment of the present teaching. Relative abundances of *Lactobacillus salivarius* MLGs in fecal, dental and salivary are plotted, and the difference between very active and moderately active RA cases is significant in the fecal and dental samples (p=0.017, 0.036, 0.084 respectively, Wilcoxon rank-sum test). MLG identification numbers are indicated in parentheses after the annotations. The disease classification followed the European League Against Rheumatism (EULAR) criterion, i.e. 3.2<DAS28≤5.1, moderate; DAS28>5.1, very active (Table 4).

One can compute correlations between the relative abundances of fecal, dental and salivary MLGs among samples (n=69). This may help to better understand the distribution of RA-associated bacteria across body sites. *L. salivarius* from the three sites (*Lactobacillus* sp. in the gut) showed positive correlation with each other (Table 5), confirming presence of the bacterium in multiple body sites.

If classification based on two sites was used to overrule the few misclassifications based on the other site, none of the subjects were misclassified except for one related control, highlighting the power of examining the microbiome at multiple sites (Table 6). Moreover, these results indicate that fecal, dental and salivary microbial markers could all be highly useful for the diagnosis and management of RA, while the dental microbiome (with probability of RA 0.94) might be more sensitive than the gut microbiome (with probability of RA 0.73).

Figure 6:
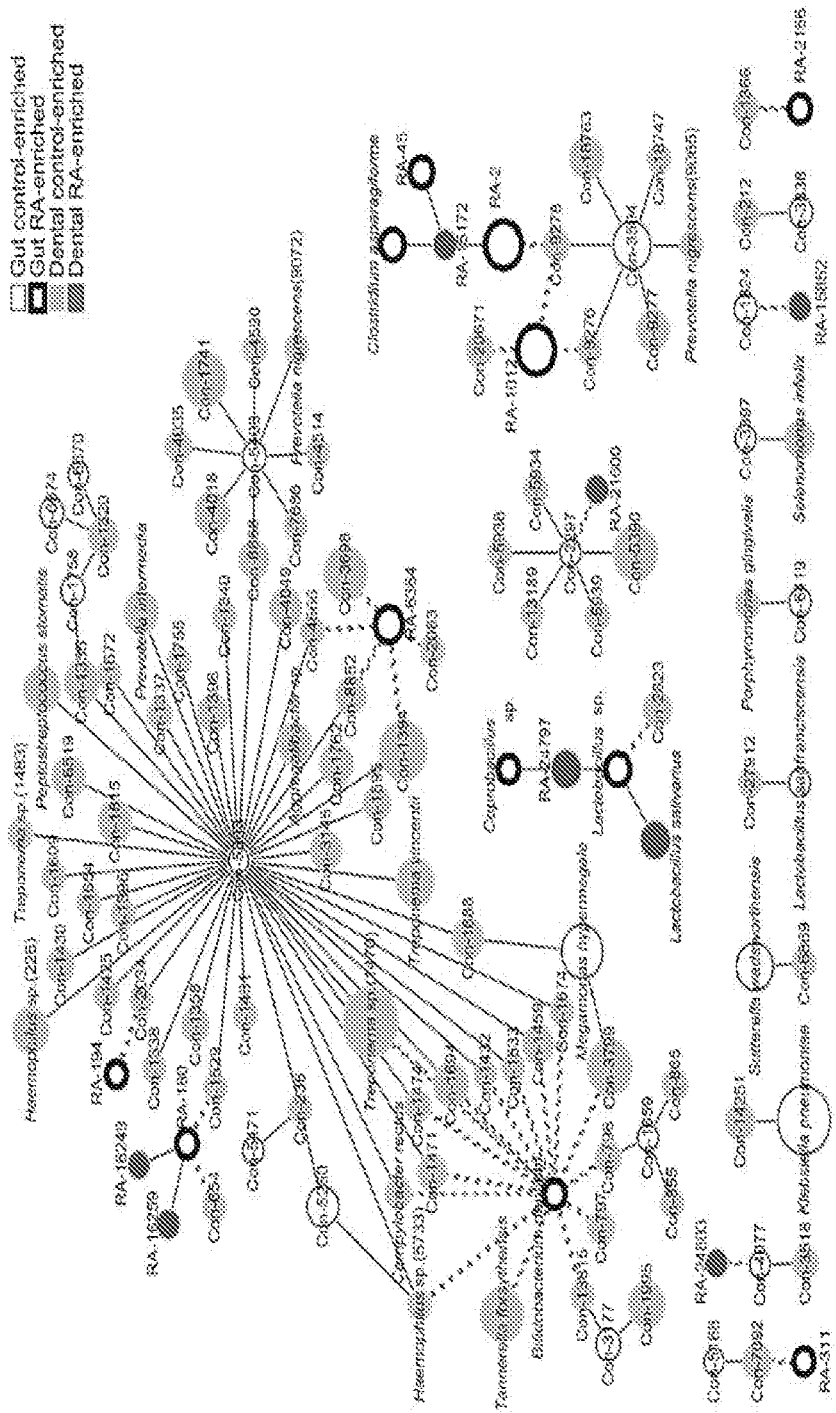
FIG. 6 shows correlations between the relative abundances of gut and dental MLGs, according to an embodiment of the present teaching.
Figure 7:
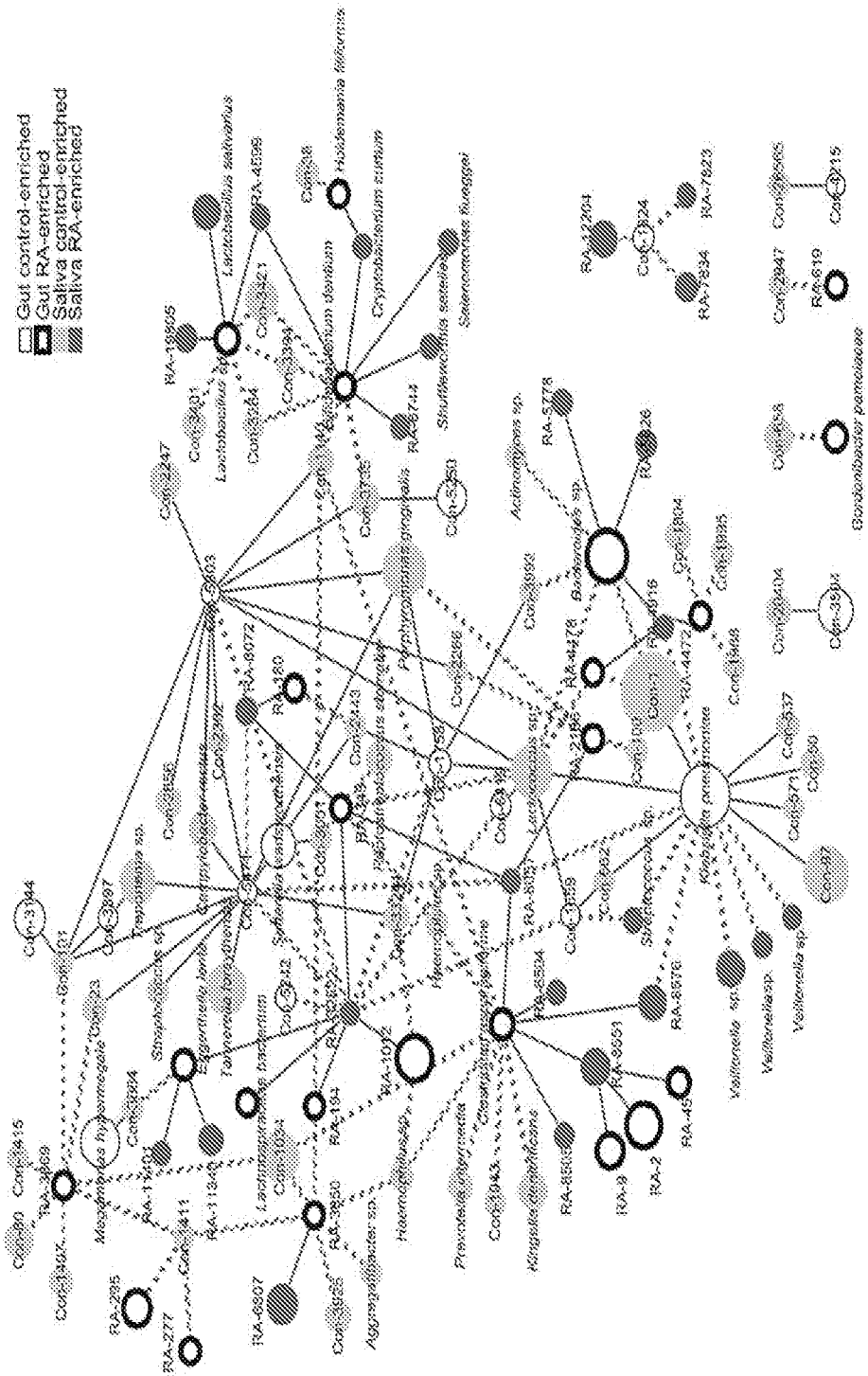
FIG. 7 shows correlations between the relative abundances of gut and salivary MLGs, according to an embodiment of the present teaching.
Figure 8:
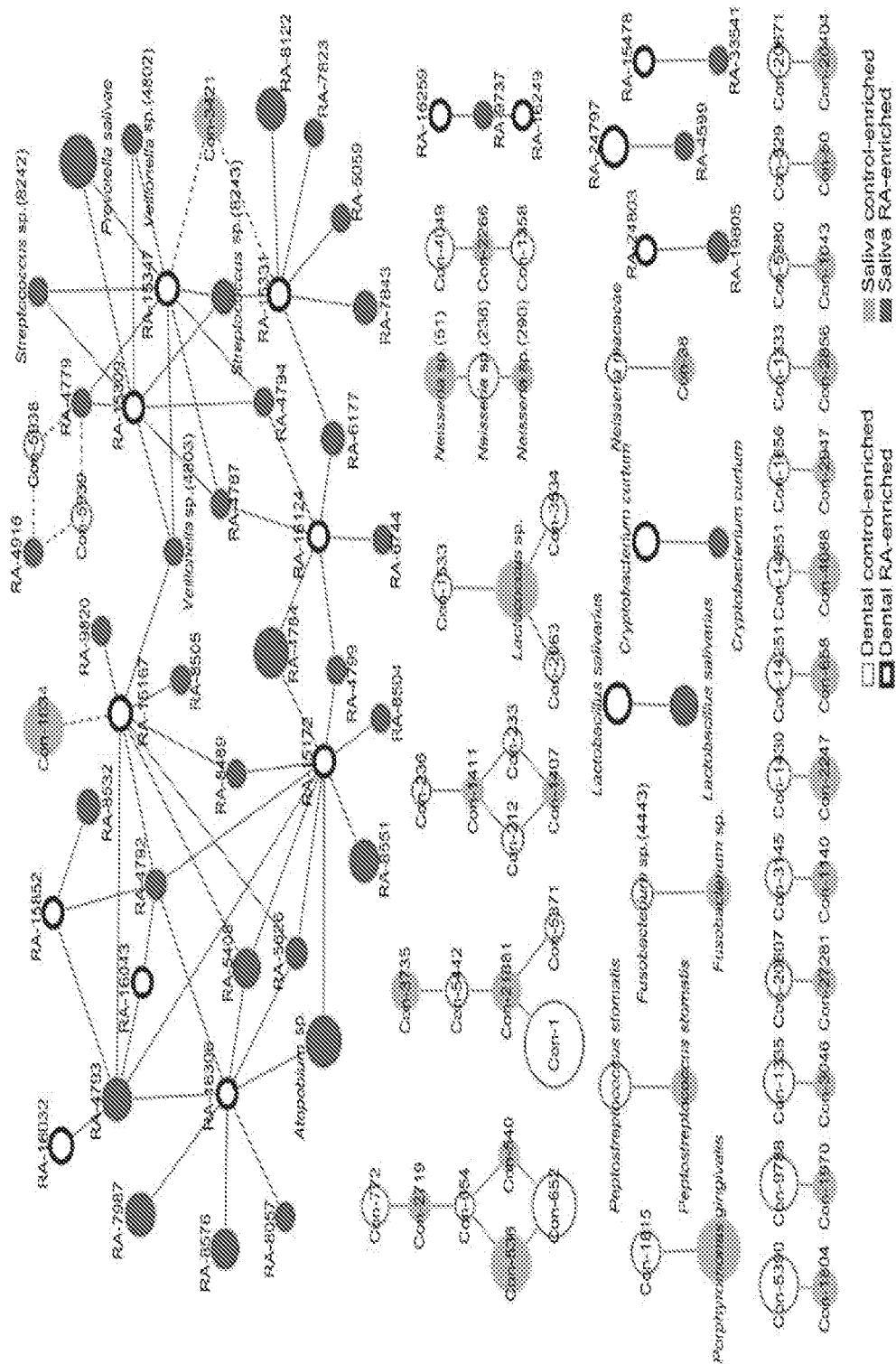
FIG. 8 shows correlations between the relative abundances of dental and salivary MLGs, according to an embodiment of the present teaching.

FIGS. 6-8 show correlation between gut and oral MLGs. FIG. 6 shows correlations between the relative abundances of gut and dental MLGs, according to an embodiment of the present teaching. FIG. 7 shows correlations between the relative abundances of gut and salivary MLGs, according to an embodiment of the present teaching. According to both FIG. 6 and FIG. 7, Spearman's correlation between the relative abundances of gut and dental or salivary MLGs (>100 genes) were calculated for subjects with the full set of fecal, dental and salivary samples (n=69). Similar correlations were observed using other measures, i.e. TIGRESS (Trustful Inference of Gene Regulation using Stability Selection), Boruta, CLR (Context Likelihood of Relatedness), Bicor (Biweight midcorrelation), MINE (Maximal Information Nonparametric Exploration). Size of the nodes reflects number of genes in each MLG. MLGs were colored according to body site and direction of enrichment. MLG identification numbers are listed in parentheses if more than one MLG annotated to the same species or unclassified species in a genus (sp.). Possible strain names are listed in Table 2-1 for all MLGs with more than 50% of genes annotated to the strain(s), even if the criteria for pinpointing a species or a genus has not been met. Solid lines (edges) represent Spearman's correlation coefficient (cc)>0.4, p<0.05; dotted lines (edges) represent cc<−0.4, p<0.05.

FIG. 8 shows correlations between the relative abundances of dental and salivary MLGs, according to an embodiment of the present teaching. In accordance with FIG. 8, MLGs were colored according to body site and direction of enrichment. MLG identification numbers are listed in parentheses if more than one MLG annotated to the same species or unclassified species in a genus (sp.). Possible strain names are listed in Table 2-1 for all MLGs with more than 50% of genes annotated to the strain(s), even if the criteria for pinpointing a species or a genus has not been met. Solid lines (edges) represent Spearman's correlation coefficient (cc)>0.6, p<0.05; dotted lines (edges) represent cc<−0.6, p<0.05.

Figure 9:
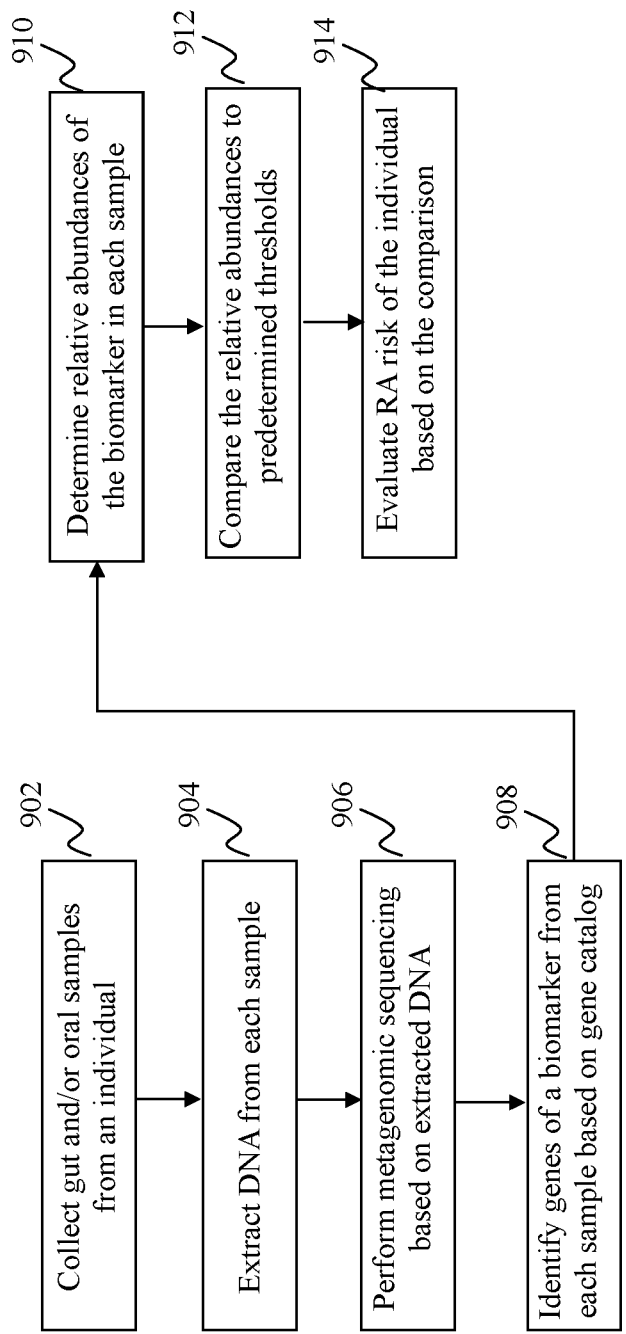
FIG. 9 shows a flowchart of an exemplary process in which a biomarker is utilized for evaluating RA risk, according to an embodiment of the present teaching.

FIG. 9 shows a flowchart of an exemplary process in which a biomarker is utilized for evaluating RA risk, according to an embodiment of the present teaching. First, gut and/or oral samples are collected at 902 from an individual to evaluate RA risk of the individual. The gut samples may include fecal samples, while the oral samples may include dental and salivary samples. DNA extraction is performed on each sample at 904. The extracted DNA is sequenced, e.g. by a metagenomic sequencing at 906, to obtain sequences of the DNA. In one embodiment, the sequences of the DNA may be obtained by polymerase chain reaction (PCR) with a primer that hybridizes to at least some of the DNA. In another embodiment, the sequences of the DNA may be obtained by using one or more probes that specifically recognize at least some of the DNA.

Then at 908, genes of a biomarker are identified from each sample based on gene catalog. For example, the biomarker may be RA-enriched MLGs, e.g. *Clostridium asparagiforme, Bacteroides* sp. and *Lactobacillus* sp. (most related to *L. salivarius*) and/or anaerobes such as *Lactobacillus salivarius, Atopobium* sp. and *Cryptobacterium curtum*. In one embodiment, *Lactobacillus salivarius* is a preferred biomarker for evaluating RA risk. The term "gene" as used in the present teaching may refer to any DNA sequence.

Relative abundances of the biomarker in each sample are determined at 910. For example, one can list genes of the biomarker among the sequences of the DNA in a sample in order of the genes' respective relative abundances. After removing the top 5% genes with highest relative abundance and the bottom 5% genes with lowest relative abundance, relative abundances of the remaining genes of the biomarker can be averaged or fit with a Poisson distribution to determine a relative abundance of the biomarker in the sample.

At 912, the relative abundances are compared to predetermined thresholds. A predetermined threshold may be associated with a type of sample, e.g. fecal, dental or salivary samples, and determined based on statistics analysis related to the biomarker. RA risk of the individual is evaluated based on the comparisons at 914. For example, as *L. salivarius* is more abundant in very active (DAS28>5.1) RA cases compared to mild-to-moderately active (DAS28≤5.1) RA cases, the threshold may be set as a relative abundance of *L. salivarius* that corresponds to DAS28=5.1. Then, RA risk of the individual is high if the relative abundance of the *L. salivarius* is higher than the threshold. In another embodiment, the relative abundances of different types of samples may be combined to evaluate RA risk.

Various exemplary thresholds of MLG relative abundance for classification are listed in Table 6, for different types of samples. When MLG relative abundance is larger than the threshold, the person is at risk of RA.

In another embodiment, RA risk can be evaluated based on a classifier that is generated based on a training set. For a given relative abundance of a biomarker, the classifier can indicate a probability of an individual having RA. The training set may comprise relative abundances of the biomarker in samples from a plurality of subjects having RA and a plurality of subjects not having RA. The classifier may be generated based on a Multivariate statistical model, e.g. a randomForest model. For example, for a certain relative abundance of a biomarker, a corresponding probability of RA can be determined based on the classifier. Then, the RA risk of the individual can be evaluated based on the probability. For example, the probability greater than a predetermined threshold indicates that the subject has or is at risk of having RA.

DMARD treatment's modification of the RA microbiome is described as below. One may compute MLGs before and after treatment (for 3 months, except for 6 samples) in fecal samples from 40 individuals (Table 1-3). This may help to examine whether the treatment by DMARD restores a healthy microbiome. Most of the patients received the anchor drug methotrexate (MTX), the traditional Chinese medicinal component *Tripterygium wilfordii* (thunder god vine) glycosides (T2), or both (MTX+T2) as DMARD. Before-treatment or RA-enriched MLGs such as BDM-3355 (BDM, Before DMARD) and *Bacteroides* sp. (with motifs similar to collagen XI and HLA-DR4/1) were more diminished after treatment with T2 than with MTX or MTX+T2, while after-treatment-enriched MLGs such as ADM-2636 (most related to *Escherichia coli*) and ADM-2944 (ADM, After DMARD) were more increased after T2. But the use of MTX or MTX+T2 may be better in other aspects, e.g. higher levels of *Bacteroides caccae* and *Haemophilus* sp. These data can indicate that different DMARD modulates the gut microbiome differently, and may suggest that surveying the gut microbiome would help optimize the choice of DMARD and auxiliary therapies.

DMARD treatment showed promising modulation of the oral microbiome as well, with some of the control-enriched dental or salivary MLGs e.g. *Aggregatibacter* sp. over-represented in patients with good response compared to those with moderate or no improvement. Control-enriched dental MLGs such as Con-16138, *Prevotella intermedia* were most abundant in patients treated with MTX+T2 compared to T2 alone or MTX alone, while RA-9938, RA-10684 and RA-9998 were most reduced in patients treated with MTX alone. Differential modulations of RA- or control-associated MLGs by MTX, MTX+T2 or T2 were also observed in the saliva samples. Notably, no significant difference in *Lactobacillus salivarius* was detected in any of the above-mentioned comparisons, indicating that the gut and oral microbiome were still not exactly healthy after treatment. Thus, both the gut and the oral microbiome respond partially to DMARD and should be managed according to the severity of RA and the DMARD of choice.

Figure 10:
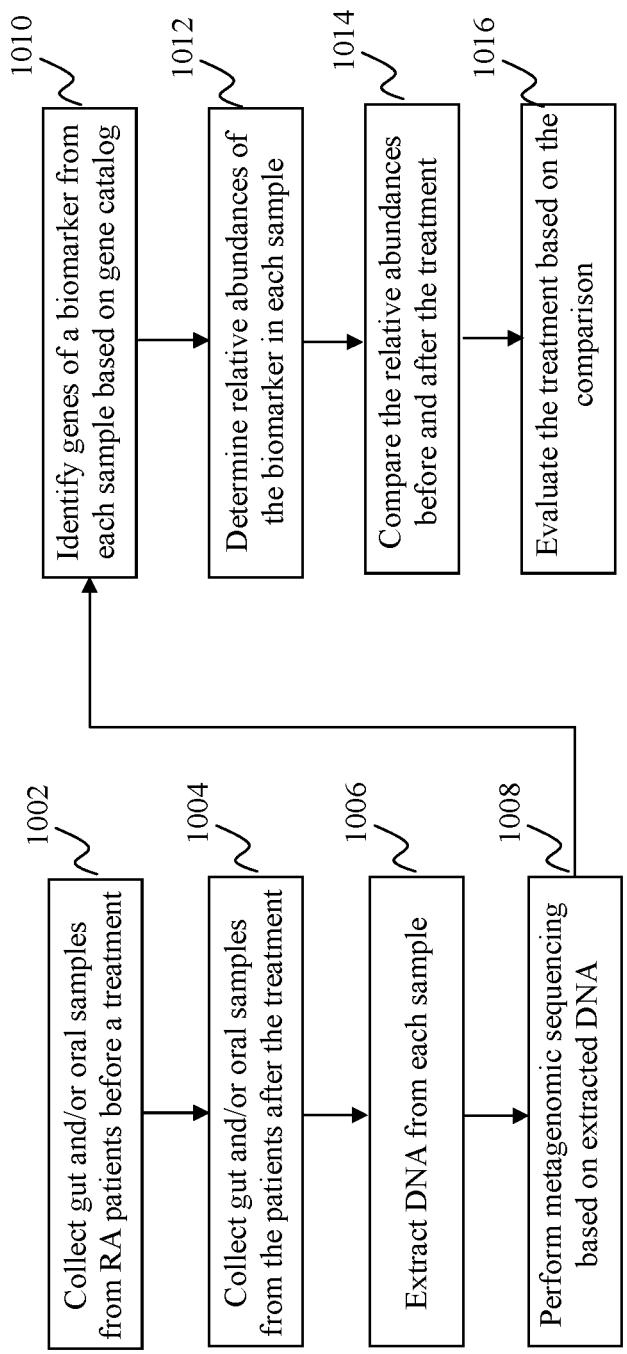
FIG. 10 shows a flowchart of an exemplary process in which a biomarker is utilized for evaluating a treatment regarding RA, according to an embodiment of the present teaching.

FIG. 10 shows a flowchart of an exemplary process in which a biomarker is utilized for evaluating a treatment regarding RA, according to an embodiment of the present teaching. First, gut and/or oral samples are collected at 1002 from RA patients before a treatment. The gut samples may include fecal samples, while the oral samples may include dental and salivary samples. As discussed before, the treatment may be a DMARD treatment like MTX, T2, or MTX+T2, or may be any treatment regarding RA. At 1004, gut and/or oral samples are collected from the same RA patients after they receive treatment. DNA extraction is performed on each sample at 1006. The extracted DNA is sequenced at 1008, e.g. by a metagenomic sequencing, to obtain sequences of the DNA. In one embodiment, the sequences of the DNA may be obtained by PCR with a primer that hybridizes to at least some of the DNA. In another embodiment, the sequences of the DNA may be obtained by using one or more probes that specifically recognize at least some of the DNA.

Then at 1010, genes of a biomarker are identified from each sample based on gene catalog. For example, the biomarker may be RA-enriched MLGs, e.g. *Clostridium asparagiforme*, *Bacteroides* sp. and *Lactobacillus* sp. (most related to *L. salivarius*) and/or anaerobes such as *Lactobacillus salivarius*, *Atopobium* sp. and *Cryptobacterium curtum*. In one embodiment, *Lactobacillus salivarius* is a preferred biomarker for evaluating a treatment regarding RA.

Relative abundances of the biomarker in each sample are determined at 1012. For example, one can list genes of the biomarker in a sample in order of their respective relative abundances. After removing the top 5% genes with highest relative abundance and the bottom 5% genes with lowest relative abundance, relative abundances of the remaining genes of the biomarker can be averaged or fit with a Poisson distribution to determine a relative abundance of the biomarker in the sample. This may be performed for samples before and after the treatment.

At 1014, one can compare the relative abundances of the biomarker before and after the treatment for each RA patient. For example, the relative abundances of *L. salivarius* in a same type of sample (e.g. fecal, dental or salivary samples) may be determined both before a RA patient receives the treatment and after the RA patient receives the treatment. Then, the relative abundances before and after the treatment may be compared to see whether *L. salivarius* is less abundant after the treatment. If so, the treatment shows some effect at least on this patient. Similar comparisons can be performed on all RA patients with collected samples.

The treatment is then evaluated based on the comparison(s) at 1016. For example, for all RA patients in evaluation, the relative abundances of *L. salivarius* before and after the treatment can be compared to see whether *L. salivarius* is less abundant after the treatment. In one embodiment, if relative abundance of *L. salivarius* is reduced after the treatment for more than a given percentage of the RA patients, the treatment may be determined to be effective. In another embodiment, if the average relative abundance of *L. salivarius* among the RA patients decreases by a given number after the treatment, the treatment may be determined to be effective.

In another embodiment, a treatment regarding RA may be evaluated merely based on the sample collected from the RA patients after the treatment. In that case, the relative abundances of the biomarker, e.g. *L. salivarius*, can be calculated for all patients after the treatment. Then, the relative abundances can be compared with a predetermined threshold to determine whether the treatment brings down the relative abundance of the biomarker to a safe range that indicates no or low RA risk. If so, the treatment may be evaluated as effective. The treatment may also be evaluated with a classifier.

In accordance with various embodiments, a biomarker, e.g. *L. salivarius*, may have different uses. The present disclosure includes but not limited to: *L. salivarius* for use as a biomarker; *L. salivarius* for use as a measurable indicator of RA; *L. salivarius* for use of evaluating or predicting risk of RA in a subject; *L. salivarius* for use of diagnosing RA in a subject; and *L. salivarius* for use of evaluating a treatment regarding a disease, e.g. RA.

In one example, a biomarker may be used for evaluating or predicting risk of RA in a subject to be tested. A sample is collected from the subject. DNA is extracted from the sample. Sequences of the DNA are obtained. Then, a relative abundance of the biomarker is calculated based on the sequences of the DNA. The biomarker may comprise a DNA sequence in a genome of *Lactobacillus salivarius*. A probability of the subject having a disease can be obtained based on the relative abundance. The risk of RA in the subject may be evaluated or predicted based on the probability.

In another example, a biomarker may be used for evaluating a treatment regarding a disease, e.g. RA. For each subject of a plurality of subjects having the disease, a sample from the subject is collected after the subject receives the treatment. DNA is extracted from the sample. Sequences of the DNA are obtained. Then, a relative abundance of the biomarker is calculated based on the sequences of the DNA. The biomarker may comprise a DNA sequence in a genome of *Lactobacillus salivarius*. The treatment may be evaluated based on the relative abundances calculated for the plurality of subjects.

In yet another example, a biomarker may be used for evaluating a treatment regarding a disease, e.g. RA. For each subject of a plurality of subjects having the disease, a first sample is collected from the subject before the subject receives the treatment, and a second sample is collected from the subject after the subject receives the treatment. A first relative abundance of a biomarker is calculated based on the first sample. A second relative abundance of the biomarker is calculated based on the second sample. The biomarker comprises a DNA sequence in genome of *Lactobacillus salivarius*. The treatment may then be evaluated based on the first relative abundances and the second relative abundances calculated for the plurality of subjects.

According to an embodiment of the present disclosure, a biomarker for evaluating a treatment regarding a disease, e.g. RA, comprises a DNA sequence in a genome of *Lactobacillus salivarius*. According to various embodiments of the present disclosure, the biomarker for evaluating a treatment regarding a disease, e.g. RA, may comprise at least a partial sequence of SEQ ID NO: 1 to 593; SEQ ID NO: 594 to 1536; or SEQ ID NO: 1537 to 2594, as stated in Table 2-2. The sequence listing submitted herewith includes nucleotide and/or amino acid sequences corresponding to the above mentioned SEQ IDs.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

TABLE 1-1

Samples used for gene catalog construction

| Group | | case | control | total number |
|---|---|---|---|---|
| Samples used for gene catalog construction | fecal samples | 115 (including 21 from DMARD-treated patients) | 97 | 212 |
| | dental plaques samples | 54 | 51 | 105 |
| | saliva samples | 51(including 4 from DMARD-treated patients) | 47 | 98 |

TABLE 1-2

Sample information of training sets (chosen from samples used for gene catalog construction in Table 1-1)

| Group | | case | control | total number |
|---|---|---|---|---|
| Training sets | fecal samples | 77 | 80 | 157 |
| | dental plaques samples | 50 | 50 | 100 |
| | saliva samples | 47 | 47 | 94 |

TABLE 1-3

Sample information of test sets

| Group | | case | control | total number |
|---|---|---|---|---|
| Test sets | fecal samples | 17 | 17 | 34 |
| | fecal samples | 40(DMARD-treated patients) | — | 40 |
| | dental plaques samples | 37(DMARD-treated patients) | — | 37 |
| | saliva samples | 24(DMARD-treated patients) | — | 24 |

TABLE 2-1 fecal, dental and salivary MLGs

| | gut MLG | dental MLG | salivary MLG |
|---|---|---|---|
| MLG ID | 2169 | 16600 | 4643 |
| P-value | 1.16E−03 | 2.13E−04 | 5.72E−04 |
| Enrichment (1, case; 0, control) | 1 | 1 | 1 |
| Gene number (>=30) | 593 | 943 | 1058 |
| Case occurrence | 0.44 | 0.48 | 0.61 |
| Control occurrence | 0.21 | 0.18 | 0.28 |
| Abundance mean in all cases | 1.40E−07 | 3.67E−07 | 1.91E−07 |
| Abundance mean in all controls | 8.50E−08 | 4.79E−09 | 4.72E−08 |
| Abundance mean in cases that contained the MLG | 3.16E−07 | 7.63E−07 | 3.14E−07 |
| Abundance mean in controls that contained the MLG | 4.00E−07 | 2.71E−08 | 1.71E−07 |

TABLE 2-1-continued fecal, dental and salivary MLGs

|  | gut MLG | dental MLG | salivary MLG |
|---|---|---|---|
| Odds Ratio (95% CI) | 1.09 (0.78, 1.52) | 222562231.41 (0.02, 2859615161906952192) | 1.93 (0.73, 5.07) |
| MLG annotation (95% identity for species, 85% identity for genus) | Lactobacillus sp. | Lactobacillus salivarius | Lactobacillus salivarius |
| Possible strain 1 | Lactobacillus salivarius CECT 5713 | Lactobacillus salivarius CECT 5713 | Lactobacillus salivarius CECT 5713 |
| # genes annotated to strain (65% identity) | 504 | 897 | 988 |
| Fraction genes annotated to strain | 0.850 | 0.951 | 0.934 |
| Average identity (%) | 98.78 | 99.81 | 99.81 |
| Possible strain 2 | Lactobacillus salivarius ACS-116-V-Col5a | Lactobacillus salivarius UCC118 | Lactobacillus salivarius ACS-116-V-Col5a |
| # genes annotated to strain (65% identity) | 499 | 750 | 818 |
| Fraction genes annotated to strain | 0.841 | 0.795 | 0.773 |
| Average identity (%) | 98.69 | 98.92 | 98.99 |
| Possible strain 3 | Lactobacillus salivarius HO66, ATCC 11741 | Lactobacillus salivarius ACS-116-V-Col5a | Lactobacillus salivarius UCC118 |
| # genes annotated to strain (65% identity) | 490 | 741 | 809 |
| Fraction genes annotated to strain | 0.826 | 0.786 | 0.765 |
| Average identity (%) | 98.64 | 98.98 | 98.97 |

TABLE 2-2

SEQ ID of the fecal, dental and salivary MLGs

| MLG ID | SEQ ID NO: | gene number |
|---|---|---|
| mlg_id: 2169 | 1~593 | 593 |
| mlg_id: 16600 | 594~1536 | 943 |
| mlg_id: 4643 | 1537~2594 | 1058 |

TABLE 3

Statistics of the Lactobacillus sp. assemblies.

| Assembly | scaftigs | Total length (bp) | gaps | Average length (bp) | N50 (bp) | N90 (bp) | Max (bp) | Min (bp) | GC content (%) |
|---|---|---|---|---|---|---|---|---|---|
| Before | 42 | 1916673 | NA | 45635.07 | 109309 | 24416 | 332613 | 622 | 32.59 |
| Loop 1 | 46 | 1929732 | 333 | 41950.7 | 109513 | 24424 | 327455 | 225 | 32.62 |
| Loop 2 | 48 | 1960062 | 707 | 40834.6 | 109613 | 24415 | 660567 | 203 | 32.66 |
| Corrected | 46 | 1929666 | 0 | 41949.3 | 109513 | 24424 | 327432 | 225 | 32.62 |

TABLE 4

Relative abundances of Lactobacillus salivarius MLGs in fecal, dental and salivary samples

| Relative abundances in fecal samples | | | Relative abundances in dental samples | | | Relative abundances in salivary samples | | |
|---|---|---|---|---|---|---|---|---|
| fecal-Sample | Abundance(lg10) | DAS28 | Dental-Sample | Abundance(lg10) | DAS28 | Saliva-Sample | Abundance(lg10) | DAS28 |
| D98 | −9 | 7.79868052 | D100 | −9 | 3.42175802 | D100 | −9 | 3.421758017 |
| D93 | −6.611867753 | 7.6226307 | D102 | −9 | 4.8480466 | D104 | −5.453765687 | 8.529890674 |
| D90 | −6.191158497 | 3.96041196 | D104 | −6.040186126 | 8.52989067 | D108 | −6.806143016 | 8.473621894 |
| D86 | −8.057385587 | 6.92415126 | D108 | −7.980872312 | 8.47362189 | D113 | −9 | 4.729856872 |
| D82 | −9 | 7.13190469 | D113 | −9 | 4.72985687 | D114 | −9 | 6.853552298 |
| D80 | −9 | 6.76503311 | D114 | −9 | 6.8535523 | D117 | −9 | 7.920189059 |
| D79 | −9 | 4.0279844 | D117 | −9 | 7.92018906 | D118 | −6.042913878 | 5.312956797 |
| D77 | −7.366135759 | 6.39025936 | D118 | −6.934469737 | 5.3129568 | D121 | −9 | 6.642354428 |
| D73 | −6.383737346 | 8.40886812 | D121 | −9 | 6.64235443 | D122 | −6.91342831 | 7.996274077 |
| D69 | −9 | 5.37571817 | D122 | −8.016378923 | 7.99627408 | D124 | −9 | 6.340241035 |

TABLE 4-continued

Relative abundances of *Lactobacillus salivarius* MLGs in fecal, dental and salivary samples

| Relative abundances in fecal samples | | | Relative abundances in dental samples | | | Relative abundances in salivary samples | | |
|---|---|---|---|---|---|---|---|---|
| fecal-Sample | Abundance(lg10) | DAS28 | Dental-Sample | Abundance(lg10) | DAS28 | Saliva-Sample | Abundance(lg10) | DAS28 |
| D64 | −9 | 5.54410235 | D124 | −9 | 6.34024104 | D126 | −8.389174221 | 5.713773541 |
| D60 | −7.445724768 | 3.97640265 | D126 | −8.948624905 | 5.71377354 | D130 | −7.289872807 | 5.123969264 |
| D57 | −7.796649862 | 8.19776002 | D130 | −7.319871381 | 5.12396926 | D132 | −6.917376771 | 6.888682261 |
| D55 | −6.528149782 | 6.18476371 | D132 | −7.914671086 | 6.88868226 | D133 | −6.112482915 | 6.330335876 |
| D53 | −7.734095793 | 6.94704402 | D144 | −8.481614523 | 7.94002895 | D135 | −9 | 6.155991353 |
| D44 | −6.382198292 | 5.50022386 | D145 | −7.353369588 | 5.33562662 | D144 | −7.761404179 | 7.940028946 |
| D41 | −6.133536313 | 8.01285296 | D147 | −4.810120267 | 6.54878405 | D145 | −6.463645065 | 5.335626622 |
| D33 | −9 | 8.46060172 | D15 | −9 | 7.0018003 | D147 | −5.698438864 | 6.548784045 |
| D31 | −9 | 5.31457462 | D150 | −9 | 7.42699601 | D15 | −7.613225033 | 7.001800303 |
| D29 | −9 | 5.07110729 | D157 | −8.403261181 | 5.77013589 | D150 | −9 | 7.426996005 |
| D264 | −7.876604295 | 7.68636877 | D158 | −6.48957812 | 7.3559855 | D158 | −8.036378515 | 7.3559855 |
| D255 | −9 | 3.35880461 | D166 | −9 | 4.68402861 | D166 | −9 | 4.684028613 |
| D246 | −9 | 5.50895943 | D172 | −9 | 6.56338253 | D172 | −9 | 6.56338253 |
| D235 | −9 | 5.36245034 | D177 | −8.062208673 | 4.11058331 | D173 | −9 | 4.753267564 |
| D226 | −9 | 3.75826991 | D178 | −9 | 5.89379791 | D177 | −7.764858329 | 4.110583305 |
| D225 | −9 | 5.26730818 | D179 | −7.377381185 | 5.45372598 | D178 | −9 | 5.893797906 |
| D220 | −8.256023129 | 8.19234 | D182 | −9 | 7.6346388 | D179 | −6.666584727 | 5.453725981 |
| D219 | −9 | 4.33281686 | D185 | −7.268685456 | 4.82480113 | D182 | −7.495572436 | 7.634638802 |
| D218 | −9 | 4.9372116 | D188 | −9 | 6.83496525 | D185 | −7.098613687 | 4.824801134 |
| D216 | −8.891583288 | 6.59381524 | D190 | −8.76674422 | 5.2882132 | D188 | −8.143731806 | 6.834965253 |
| D213 | −9 | 4.25625778 | D23 | −9 | 7.36348085 | D190 | −8.742451499 | 5.288213199 |
| D212 | −9 | 4.89075966 | D25 | −9 | 6.85099036 | D25 | −9 | 6.850990358 |
| D210 | −8.979008268 | 7.00624114 | D29 | −9 | 5.07110729 | D41 | −6.853197457 | 8.01285296 |
| D209 | −9 | 4.31299239 | D31 | −9 | 5.31457462 | D43 | −6.797317376 | 6.197520423 |
| D208 | −6.483913355 | 5.745 | D33 | −9 | 8.46060172 | D44 | −6.910799717 | 5.500223864 |
| D206 | −9 | 7.25794987 | D41 | −5.796743841 | 8.01285296 | D51 | −9 | 6.847803418 |
| D205 | −9 | 7.6508574 | D43 | −8.428210194 | 6.19752042 | D53 | −7.390874351 | 6.947044019 |
| D204 | −9 | 4.1459103 | D51 | −9 | 6.84780342 | D57 | −6.60695896 | 8.197760021 |
| D202 | −9 | 7.63088447 | D53 | −8.198886903 | 6.94704402 | D60 | −7.791470779 | 3.976402649 |
| D201 | −5.283022546 | 4.78379104 | D55 | −6.129609376 | 6.18476371 | D62 | −7.180662842 | 5.942224198 |
| D197 | −9 | 5.04328483 | D57 | −6.738165176 | 8.19776002 | D69 | −9 | 5.375718166 |
| D196 | −9 | 5.45729602 | D60 | −9 | 3.97640265 | D73 | −6.556695801 | 8.408868116 |
| D195 | −7.523916323 | 5.88705343 | D62 | −8.039281704 | 5.9422242 | D82 | −9 | 7.131904686 |
| D194 | −9 | 5.07491254 | D69 | −9 | 5.37571817 | D86 | −6.868622111 | 6.924151262 |
| D191 | −6.376571261 | 5.96637345 | D73 | −7.012094288 | 8.40886812 | D8_N | −9 | 5.073854483 |
| D190 | −8.662513207 | 5.2882132 | D77 | −6.835456013 | 6.39025936 | D9 | −7.736997083 | 8.574788032 |
| D188 | −8.169182242 | 6.83496525 | D79 | −9 | 4.0279844 | D90 | −8.720697158 | 3.960411962 |
| D187 | −8.31142368 | 8.59106614 | D82 | −9 | 7.13190469 | D93 | −6.901748442 | 7.6226307 |
| D185 | −7.45074993 | 4.82480113 | D86 | −7.974661284 | 6.92415126 | D94 | −9 | 5.82920269 |
| D184 | −9 | 3.58951489 | D89 | −9 | 5.377 | D98 | −9 | 7.798680516 |
| D179 | −6.478104047 | 5.45372598 | D8_N | −9 | 5.07385448 | D99 | −9 | 8.242071089 |
| D178 | −9 | 5.89379791 | D9 | −8.822539013 | 8.57478803 | | | |
| D177 | −8.36954905 | 4.11058331 | D90 | −9 | 3.96041196 | | | |
| D174 | −8.450552033 | 6.58470347 | D94 | −9 | 5.82920269 | | | |
| D173 | −9 | 4.75326756 | | | | | | |
| D169 | −7.394270982 | 7.01915442 | | | | | | |
| D168 | −8.77581245 | 6.38421883 | | | | | | |
| D166 | −9 | 4.68402861 | | | | | | |
| D163 | −9 | 4.9850232 | | | | | | |
| D159 | −8.762169575 | 6.28026633 | | | | | | |
| D158 | −9 | 7.3559855 | | | | | | |
| D157 | −9 | 5.77013589 | | | | | | |
| D153 | −9 | 6.21962859 | | | | | | |
| D141 | −9 | 6.49456205 | | | | | | |
| D138 | −8.908362017 | 7.33999124 | | | | | | |
| D135 | −8.697956283 | 6.15599135 | | | | | | |
| D134 | −9 | 4.75253438 | | | | | | |
| D133 | −7.661497584 | 6.33033588 | | | | | | |
| D132 | −9 | 6.88868226 | | | | | | |
| D121 | −9 | 6.64235443 | | | | | | |
| D118 | −5.847384965 | 5.3129568 | | | | | | |
| D114 | −9 | 6.8535523 | | | | | | |
| D113 | −9 | 4.72985687 | | | | | | |
| D108 | −9 | 8.47362189 | | | | | | |
| D102 | −9 | 4.8480466 | | | | | | |
| D100 | −9 | 3.42175802 | | | | | | |

TABLE 5

Spearman's correlation and best matched strain for *Lactobacillus salivarius*-like MLGs from the gut and oral sites. (Strain information as in Table 2-1.)

| | Species of interest *L. salivarius* | | |
|---|---|---|---|
| MLG ID | gut 2169 | saliva 4643 | saliva 4643 |
| MLG ID | dental 16600 | dental 16600 | gut 2169 |
| Spearman's cc | 0.5634221 | 0.8238949 | 0.7096382 |
| p-value | 4.65E−07 | 3.51E−18 | 8.73E−12 |
| MLG ID | gut 2169 | saliva 4643 | saliva 4643 |
| # genes | 593 | 1058 | 1058 |
| Possible strain 1 | *Lactobacillus salivarius* CECT 5713 | *Lactobacillus salivarius* CECT 5713 | *Lactobacillus salivarius* CECT 5713 |
| Genes annotated to strain (65% identity) | 504 | 988 | 988 |
| Fraction of genes annotated | 0.850 | 0.934 | 0.934 |
| Average identity (%) | 98.78 | 99.81 | 99.81 |
| MLG ID | dental 16600 | dental 16600 | gut 2169 |
| # genes | 943 | 943 | 593 |
| Possible strain 1 | *Lactobacillus salivarius* CECT 5713 | *Lactobacillus salivarius* CECT 5713 | *Lactobacillus salivarius* CECT 5713 |
| Genes annotated to strain (65% identity) | 897 | 897 | 504 |
| Fraction of genes annotated | 0.951 | 0.951 | 0.850 |
| Average identity (%) | 99.81 | 99.81 | 98.78 |

TABLE 6 classification results of fecal, dental and salivary MLGs in the 69 samples

| classification | gut sample | dental sample | saliva sample | combination of 3 sits samples |
|---|---|---|---|---|
| threshold* of MLG relative abundance for classification | >1.175e−9 | >5.326e−9 | >8.095e−10 | gut sample >1.175e−9, dental sample >5.326e−9 and saliva sample >8.095e−10 |
| total number over the threshold | 26 | 17 | 32 | 13 |
| RA number in total number | 19 | 16 | 23 | 12 |
| probability of RA (RA number/total number) | 0.730769231 | 0.941176471 | 0.71875 | 0.923076923 |

*When MLG relative abundance is larger than the threshold, the person is in risk of RA.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10883146B2). An electronic copy of the "Sequence Listing" will also be available from the USPTO upon request and payment of the fee set forth in 37 CFR 1.19(b)(3).

What is claimed is:

1. A method for obtaining a probability of a subject having a disease wherein the disease is rheumatoid arthritis, comprising:
    obtaining sequences of DNA extracted from a sample that is collected from the subject, wherein the sample comprises at least one of a fecal sample, a dental sample, and a salivary sample;
    calculating a relative abundance of a biomarker based on the sequences of the DNA, wherein the biomarker comprises a DNA sequence in a genome of *Lactobacillus salivarius*; and
    obtaining a probability of the subject having the disease based on the relative abundance to thereby determine that the individual has the rheumatoid arthritis,
    wherein the biomarker comprises at least one of the following metagenomic linkage groups (MLGs);
    the MLG corresponding to the fecal sample that consists of MLG ID NO: 2169;
    the MLG corresponding to the dental sample that consists of MLG ID NO: 16600; and
    the MLG corresponding to the salivary sample that consists of MLG ID NO: 4643;
    and wherein:
    the MLG ID NO: 2169 consists of SEQ ID NOs: 1-593;

the MLG ID NO: 16600 consists of SEQ ID NOs: 594-1536; and the MLG ID NO: 4643 consist of SEQ ID NOs: 1537-259, the method further comprising administering to the individual at least one disease-modifying antirheumatic drug (DMARD) to treat said rheumatoid arthritis.

2. The method of claim 1, wherein the DMARD is selected from methotrexate (MTX), *Tripterygium wilfordii* (thunder god vine) Leflunomide, prednisolone, hydroxychloroquine, and etanercept.

3. The method of claim 2, wherein the DMARD is methotrexate.

\* \* \* \* \*